(12) United States Patent
Faries, Jr. et al.

(10) Patent No.: US 7,176,030 B2
(45) Date of Patent: Feb. 13, 2007

(54) METHOD AND APPARATUS FOR ENSURING STERILITY OF DISPOSABLE MEDICAL ITEMS USED WITH MEDICAL EQUIPMENT

(75) Inventors: Durward Faries, Jr., Las Vegas, NV (US); Bruce Heymann, Vienna, VA (US); David Hendrix, Ashburn, VA (US)

(73) Assignee: O.R. Solutions, Inc., Chantilly, VA (US)

( * ) Notice: Subject to any disclaimer, the term of this patent is extended or adjusted under 35 U.S.C. 154(b) by 630 days.

(21) Appl. No.: 10/172,731

(22) Filed: Jun. 17, 2002

(65) Prior Publication Data

US 2003/0231990 A1 Dec. 18, 2003

(51) Int. Cl.
*G01N 33/00* (2006.01)

(52) U.S. Cl. .......................... 436/1; 422/105; 422/119

(58) Field of Classification Search .................. 422/58, 422/61, 50, 105, 119, 120; 436/1
See application file for complete search history.

(56) References Cited

U.S. PATENT DOCUMENTS

| | | |
|---|---|---|
| 4,647,756 A | 3/1987 | Willis |
| 5,040,699 A | 8/1991 | Gangemi |
| 5,245,693 A | 9/1993 | Ford et al. |
| 5,333,326 A | 8/1994 | Faries, Jr. et al. |
| 5,408,577 A | 4/1995 | Weber, Jr. et al. |
| 5,429,801 A | 7/1995 | Faries, Jr. et al. |
| 5,443,082 A | 8/1995 | Mewburn |
| 5,522,095 A | 6/1996 | Faries, Jr. et al. |
| 5,524,643 A | 6/1996 | Faries, Jr. et al. |
| 5,531,697 A | 7/1996 | Olsen et al. |
| 5,615,423 A | 4/1997 | Faries, Jr. et al. |
| 5,653,938 A | 8/1997 | Faries, Jr. et al. |
| 5,816,252 A | 10/1998 | Faries, Jr. et al. |
| 5,857,467 A | 1/1999 | Faries, Jr. et al. |
| 5,862,672 A | 1/1999 | Faries, Jr. et al. |
| 5,879,621 A | 3/1999 | Faries, Jr. et al. |
| 6,091,058 A | 7/2000 | Faries, Jr. et al. |
| 6,255,627 B1 | 7/2001 | Faries, Jr. et al. |
| 6,371,121 B1 * | 4/2002 | Faries et al. ................. 128/849 |

(Continued)

FOREIGN PATENT DOCUMENTS

GB 2 336 214 10/1999

(Continued)

*Primary Examiner*—Lyle A. Alexander
(74) *Attorney, Agent, or Firm*—Edell, Shapiro & Finnan, LLC

(57) ABSTRACT

A disposable medical item for use with medical equipment includes circuitry forming an electrical path between the item and medical equipment. The circuitry is coupled to a medical equipment controller or independent microprocessor and includes a fuse. The controller transmits a status signal over the path in response to the equipment receiving the item. A disabled fuse prevents traversal of the path by the status signal, thereby indicating prior item use. If the controller does not detect the status signal, medical equipment operation is disabled. Otherwise, the controller transmits over the path a signal sufficient to disable the fuse to indicate item use and verifies the disabled fuse status. If the disabled fuse status is verified, the controller enables equipment operation. The controller periodically checks the fuse status during equipment operation and disables operation in response to a prior used item inserted into the medical equipment.

21 Claims, 5 Drawing Sheets

U.S. PATENT DOCUMENTS

| | | |
|---|---|---|
| 6,649,040 B1 * | 11/2003 | Mirchi et al. ............... 205/390 |
| 6,810,881 B2 | 11/2004 | Faries, Jr. et al. |
| 6,860,271 B2 * | 3/2005 | Faries et al. ................ 128/849 |
| 6,910,485 B2 | 6/2005 | Faries, Jr. et al. |
| 6,918,395 B2 | 7/2005 | Faries, Jr. et al. |
| 2003/0075183 A1 | 4/2003 | Heymann et al. |
| 2003/0114795 A1 | 6/2003 | Fairies, Jr. et al. |
| 2004/0200480 A1 | 10/2004 | Faries, Jr. et al. |
| 2004/0200483 A1 | 10/2004 | Faries, Jr. et al. |
| 2004/0208780 A1 | 10/2004 | Fairies, Jr. et al. |

FOREIGN PATENT DOCUMENTS

| | | |
|---|---|---|
| WO | WO 93 20770 | 10/1993 |
| WO | WO 96 34572 | 11/1996 |
| WO | WO 02098311 | 12/2002 |

\* cited by examiner

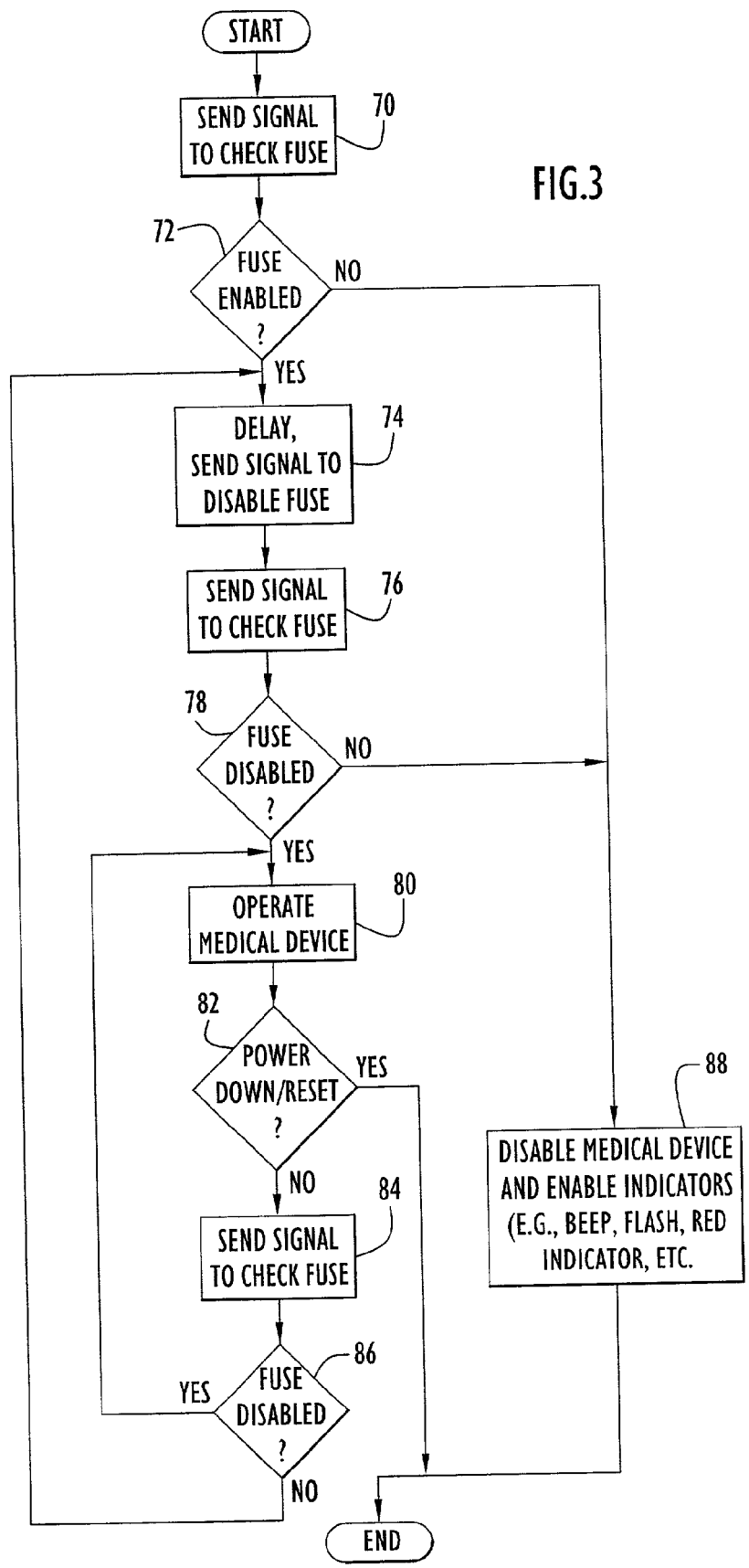

METHOD AND APPARATUS FOR ENSURING STERILITY OF DISPOSABLE MEDICAL ITEMS USED WITH MEDICAL EQUIPMENT

BACKGROUND OF THE INVENTION

1. Technical Field

The present invention pertains to medical devices employing disposable medical items. In particular, the present invention pertains to ensuring operation of medical devices with sterile disposable items to prevent contamination and injury to a patient.

2. Discussion of Related Art

The maintenance of sterile conditions during performance of medical procedures is crucial to prevent infection and injury to a patient. Accordingly, medical items utilized within a medical procedure are typically sterilized prior to performance of the procedure and maintained within a sterile field to ensure sterility. Various medical items maybe disposable in order to reduce the amount of sterilization. These items are typically limited to a single use, thereby requiring a new sterile item for each procedure. For example, a disposable surgical drape maybe employed to serve as a container and provide a sterile field for a sterile medium within a basin of a thermal treatment system. The drape is discarded after a single use and replaced with a new sterile drape for each procedure. Further, disposable IV fluid cassettes or delivery sets may be employed during infusion of fluids into a patient. These items are similarly discarded after a single use and replaced for each procedure. Although disposable medical items are intended for a single use, there is no assurance that carelessness will not result in operation of medical devices with a prior used or non-sterile item, thereby contaminating medical procedures and risking serious injury to patients.

The related art has attempted to overcome the aforementioned problem by providing various mechanisms to determine prior use and/or detect conditions compromising sterility of medical items used with medical devices. For example, U.S. Pat. No. 5,040,699 (Gangemi) discloses a fluid compounding system wherein solution dispensing containers dispense respective fluids into a solution receiving bag via pumps under microprocessor control. The receiving bags include a bar code that is read by a bar code wand electrically connected to the system. The bar code is utilized to identify receiving bags previously used in order to prevent those receiving bags from being reused.

U.S. Pat. No. 5,524,643 (Faries, Jr. et al) discloses a method and apparatus directed toward preventing damage to drapes and heating and cooling mechanisms of a thermal treatment apparatus, and to preserving the sterile field when using such apparatus. A surgical drape is combined with a sensor, preferably attached to the drape, to detect the presence of liquid within a drape container conforming to a heating/cooling thermal treatment apparatus basin. An alternative embodiment employs sensors at opposite surfaces of the drape to measure conductance and, thereby, leakage through the drape. A microprocessor of each embodiment receives a signal representing, for example, an electrical conductance measurement and determines the presence of liquid and/or a leak. If liquid is not present or a leak is determined to exist (e.g., a drape leak enables contamination of the drape and/or liquid), the microprocessor disables a temperature controller for the basin.

U.S. Pat. No. 5,653,938 (Faries, Jr. et al) discloses an apparatus for ensuring sterility of a drape for use on surgical equipment by employing bar codes and a microprocessor. When a drape containing a bar code is placed on the corresponding surgical equipment, a bar code reader ascertains the bar code on the drape. A microprocessor receives the bar code and determines whether the bar code has been previously written to memory indicating drape prior use. If the bar code is not present, the current bar code of the drape is written into memory, and subsequent operation of the surgical equipment commences. If the bar code is present, the microprocessor prevents the surgical equipment from operating.

The related art systems described above may stand some improvement. In particular, the Gangemi and Faries Jr. et al (U.S. Pat. No. 5,653,938) systems employ bar codes to identify and determine prior item use. Thus, substantial logistics are required to ensure that a proper bar code is associated with each item to prevent erroneous prior use determinations. Further, storage of numerous item bar codes for later comparison tends to exhaust system memory and typically requires removal of bar codes or installment of additional memory. This provides system users with additional tasks, thereby increasing system operating costs and complexity. The Faries, Jr. et al sensor drape system (U.S. Pat. No. 5,524,643) detects a non-sterile drape by determining the presence of leaks within that drape. Thus, this system is limited to detecting particular circumstances or conditions that tend to contaminate drapes or render drapes non-sterile.

OBJECTS AND SUMMARY OF THE INVENTION

Accordingly, it is an object of the present invention to ensure use of sterile disposable items with medical devices.

It is another object of the present invention to prevent operation of a medical device in response to detection of a prior used or non-sterile disposable item utilized with that device.

Yet another object of the present invention is to employ a circuit within a disposable medical item including a selectively disruptable electrical path to indicate prior use of the item and to facilitate control of medical device operation accordingly.

The aforementioned objects maybe achieved individually and/or in combination, and it is not intended that the present invention be construed as requiring two or more of the objects to be combined unless expressly required by the claims attached hereto.

According to the present invention, a disposable medical item for use with medical equipment includes circuitry forming an electrical path or circuit between the item and medical equipment. The circuitry is coupled to a medical equipment controller or independent microprocessor and typically includes a fuse. The controller generates a status signal for transmission over the electrical path or circuit in response to the equipment receiving the item. A disabled fuse prevents traversal of the circuit by the status signal, thereby indicating prior use of the item. If the controller does not detect the status signal (e.g., indicating a disabled fuse and reuse of an item), medical equipment operation is disabled. When the controller detects the status signal after traversing the circuit (e.g., indicating an enabled fuse of a new and sterile item), the controller generates and transmits over the circuit a signal of a magnitude sufficient to disable the fuse.

Subsequent transmission of the disablement signal, the controller checks the fuse status by transmitting and detecting the status signal as described above. When the status signal is detected after transmission of the disablement signal, this typically indicates a prior used item employing a conductive member (e.g., coin) in place of the fuse and equipment operation is disabled. If the status signal is not detected by the controller subsequent transmission of the disablement signal (e.g., indicating a disabled fuse), the controller enables operation of the system and repeatedly determines the status of the fuse in the manner described above. When a status signal is detected during system operation (e.g., indicating either a new sterile item or a reused item employing a conductive member), the controller transmits the disablement signal and determines the fuse status to identify the nature of the event and control system operation accordingly as described above. Thus, the present invention prevents utilization of a prior used or non-sterile item with medical equipment.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

BRIEF DESCRIPTION OF THE DRAWINGS

FIG. 3 is a procedural flow chart illustrating the manner in which prior use or sterility of a disposable medical item is determined according to the present invention.

DETAILED DESCRIPTION OF THE PREFERRED EMBODIMENTS

Figure 1:
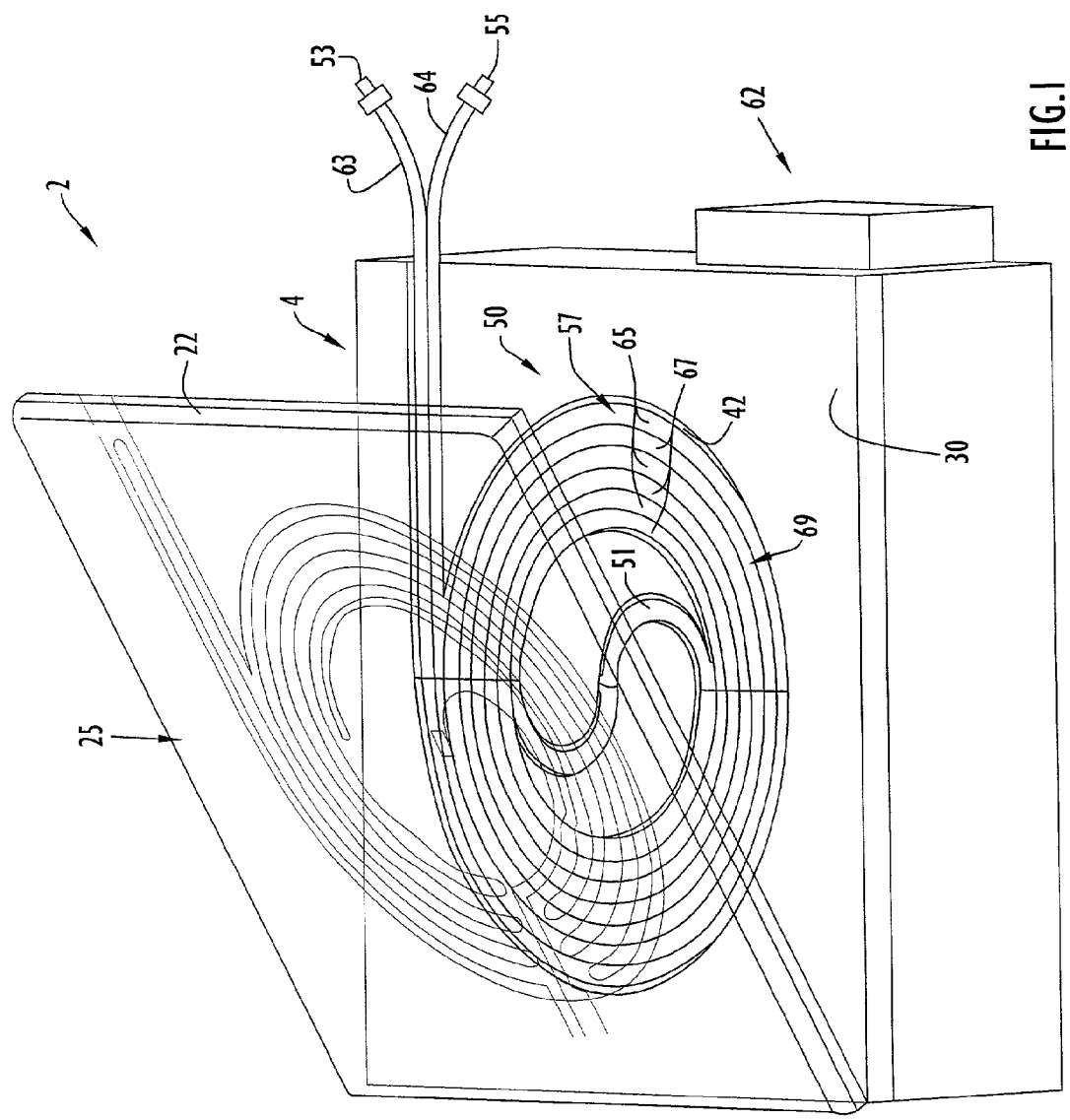
FIG. 1 is a perspective view of exemplary medical equipment in the form of an IV line temperature controlled warming device employing the apparatus of the present invention to determine prior use or sterility of a disposable tubing cassette or cartridge.

An apparatus according to the present invention may be used with a medical device or medical equipment to determine prior use or sterility of a disposable item utilized with the device. By way of example only, the medical device and disposable item may be implemented by an IV line temperature controlled warming device and corresponding disposable tubing cassette as illustrated in FIG. 1. Specifically, warming device 2 includes a housing 4 with a lid or cover 22 pivotally attached thereto. The warming device receives a tubing cassette or cartridge 50 that is typically connected to an intravenous line (IV) supplying intravenous solution from an IV solution bag or container to a patient. The device housing includes a base plate 30 to receive cassette 50 and a heater plate 42 disposed on the base plate beneath the cassette to heat a cassette bottom surface. An additional heater or heating element 25 is disposed on cover 22 to heat the cassette top surface. Thus, the cassette is disposed between the heater plate and cover heating elements to receive heat on opposing cassette surfaces for uniform heating of solution or other fluid flowing therein.

Cassette 50 includes a configuration compatible with the base plate to facilitate placement of the cassette within the warming device. Specifically, the cassette includes an inlet portion 63, an outlet portion 64 adjacent the inlet portion and a cassette body 57 defining a fluid flow path. The cassette body includes tubing sections 69, preferably transparent, arranged in generally circular and concentric sections 65, 67. A central serpentine tubing section 51 includes a generally 'S'-shaped configuration that basically reverses fluid flow and facilitates flow in opposing directions within adjacent concentric tubing sections 65, 67.

Inlet and outlet tubing portions 63, 64 are adjacent each other and extend tangentially from a circumferential edge of body 57. The inlet and outlet tubing portions terminate at respective inlet and outlet terminals 53, 55 that extend externally of the device housing when the cassette is received and retained within the base plate. The inlet and outlet terminals include suitable connectors (e.g., Luer locks) to connect inlet and outlet tubing portions 63, to any selected portions of an IV line. A sheet or backing (not shown) may be attached to the cassette top and/or bottom surface to secure the tubing arrangement thereon. The sheet may include an annular configuration similar to that of cassette 50, and may include tabs (not shown) disposed on the sheet at any desired locations to facilitate manipulation of the cassette relative to the warming device (e.g., facilitate insertion and removal of the cassette within the warming device).

A controller 62 is partially disposed within the housing to enable entry of desired solution temperatures and to control device operation. The warming device maybe oriented in a variety of positions (e.g., horizontally, vertically, etc.) and may be mounted to or supported by various structures (e.g., a patient arm or other body portion, swing arm, arm board, bed, bed rail, operating room or other table, IV pole, wall, floor, posts, etc.). The warming device is preferably positioned in close proximity to an infusion site of a patient in order to heat IV fluid (e.g., may heat fluid with or without skin contact), and may be portable for use in various locations. For further examples of the structure and operation of this type of warming device, reference is made to U.S. patent application Ser. No. 10/016,128, entitled "Method and Apparatus for Heating Solutions Within Intravenous Lines to Desired Temperatures During Infusion" and filed Dec. 17, 2001, the disclosure of which is incorporated herein by reference in its entirety. However, it is to be understood that the present invention may be employed by any medical device containing, treating or handling a sterile object used in a medical procedure (e.g., solutions, etc.), while the disposable item may be implemented by any item maintaining a sterile field for the sterile object (e.g., drape, liner, tubing cassette, etc.).

Figure 2:
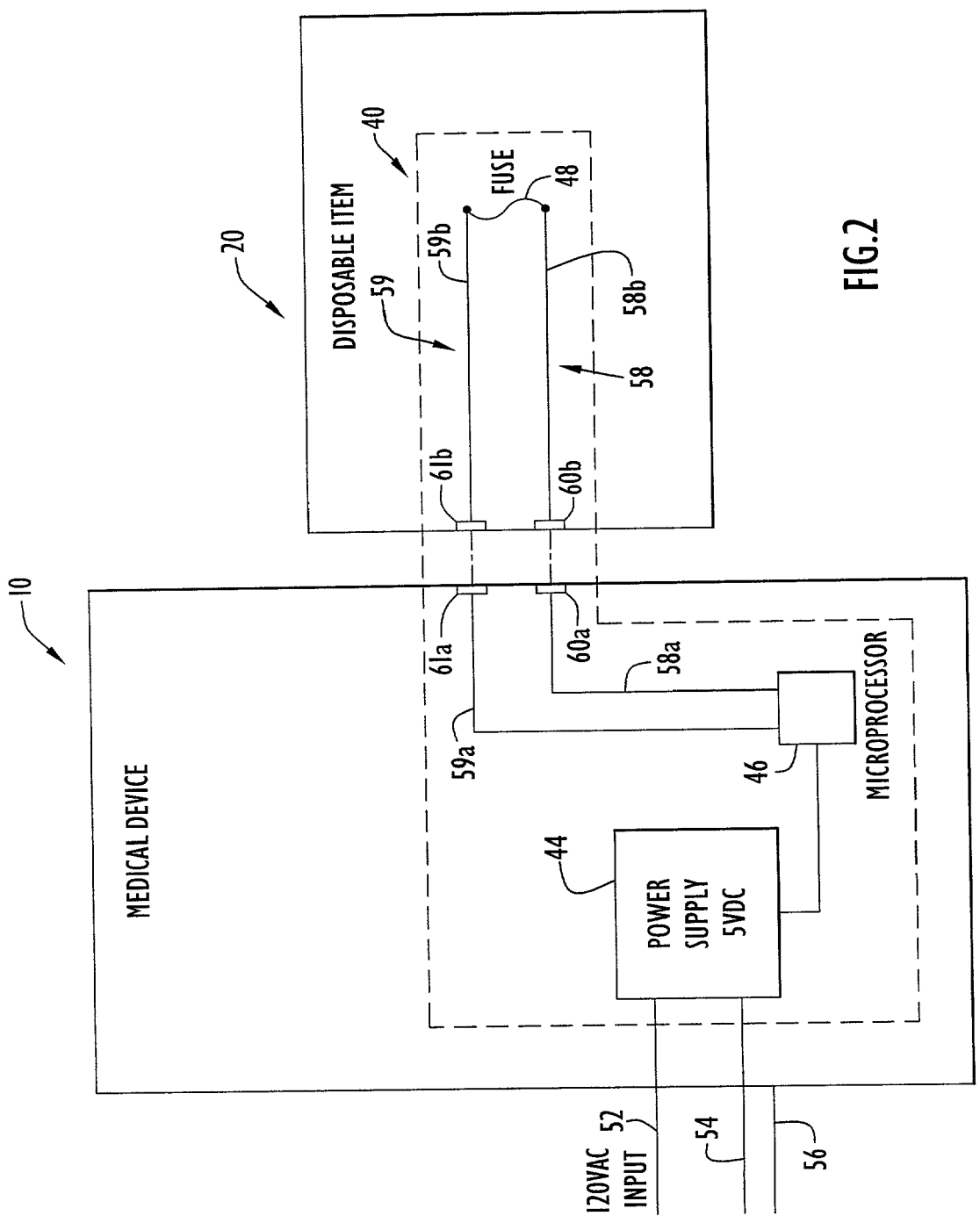
FIG. 2 is a schematic block diagram of the apparatus of the present invention determining prior use or sterility of a disposable medical item utilized with medical equipment.

Referring to FIG. 2, prior use or sterility of a disposable item is determined by a safety apparatus or circuit of the present invention. In particular, safety circuit 40 includes a power supply 44, a microprocessor or controller 46 and a fuse 48. The power supply and microprocessor are preferably implemented by conventional components and are disposed within a medical device 10 (e.g., warming device 2 or other medical device). Fuse 48 and corresponding wiring are disposed on or within disposable item 20 (e.g., tubing cassette 50 or other disposable item) as described below at any suitable locations. The fuse may include any suitable power tolerance (e.g., any voltage or current threshold) and be constructed from any suitable materials (e.g., glass fuse, thin painted metallic line, etc.). Fuse 48 is coupled to microprocessor 46 via lead wiring 58 (e.g., extending and carrying a signal from the microprocessor toward the fuse) and return wiring 59 (e.g., extending and carrying a signal from the fuse toward the microprocessor). Wiring 58, 59 basically form an electrical path or circuit between the fuse and microprocessor. Lead wiring 58 includes wire segments 58*a* and 58*b*, where segment 58*a* is disposed within the medical device and coupled to the microprocessor, while segment 58*b* is disposed on or within the disposable item and coupled to fuse 48. Similarly, return wiring 59 includes wire segments 59*a* and 59*b*, where segment 59*a* is disposed within the medical device and coupled to the microprocessor, while segment 59*b* is disposed on or within the disposable item and coupled to fuse 48.

In order to facilitate detachment or removal of the disposable item from the medical device, wire segments 58*a*, 58*b*, 59*a* and 59*b* each include a respective contact 60*a*, 60*b*, 61*a* and 61*b*. Contact 60*a* is disposed at a distal end of lead wire segment 58*a* of the medical device, while contact 60*b* is disposed at a proximal end of lead wire segment 58*b* of the disposable item. Similarly, contact 61*a* is disposed at a proximal end of return wire segment 59*a* of the medical device, while contact 61*b* is disposed at a distal end of return wire segment 59*b* of the disposable item. The item is received by the medical device with contacts 60*a*, 61*a* respectively aligned with contacts 60*b*, 61*b*, thereby coupling the medical device and disposable item wiring components to form the electrical path between the microprocessor and fuse. The contacts maybe of any shape or size, are typically constructed of metal or other conductive material, and basically couple corresponding lead and return wiring within the medical device and disposable item. Alternatively, wire segments 58*a*, 59*a* of the medical device may be coupled to corresponding wire segments 58*b*, 59*b* of the disposable item via a plug and connector type arrangement (not shown). In this case, wire segments 58*a*, 59*a* of the medical device each include a plug and/or connector, while segments 58*b*, 59*b* of the disposable item each include a corresponding plug and/or connector to couple the wire segments. The wire segments may include any conventional plugs and/or connectors or other devices to form the electrical path. The contacts, plugs, connectors, wire segments and fuse may be disposed at any suitable locations on or within the medical device and/or disposable item.

The power supply receives power from conductors 52, 54, 56 that are typically connected to a common wall outlet jack. Conductors 52, 54 preferably conduct the positive and negative potential while conductor 56 is connected to ground. The power supply converts power (e.g., 120V AC) received from the conductors into appropriate power signals (e.g., 5V DC) for the microprocessor. The microprocessor is coupled to the power supply and determines prior use or sterility of the disposable item to control device operation as described below. The safety circuit may employ a microprocessor or controller of the medical device (e.g., controller 62 of warming device 2), or include an independent microprocessor to control safety circuit operation.

The manner in which prior use or sterility of the disposable item is determined is illustrated in FIG. 3. Initially, the medical device receives a disposable item and power is enabled to facilitate operation of the device. The medical device is basically dependent upon fuse 48 (FIG. 2) of the disposable medical item being in an enabled state initially. Microprocessor 46 (FIG. 2) senses the condition of the fuse and controls medical device operation accordingly. Specifically, the microprocessor transmits a status signal (e.g., voltage, current, etc.) to the fuse at step 70 and senses that signal traversing the electrical path or circuit (e.g., wire segments and fuse). If the status signal is detected by the microprocessor on return line 59 at step 72 (e.g., indicating enablement of the fuse), the microprocessor waits a predetermined time interval (e.g., one second) and transmits a disablement signal to disable the fuse at step 74. The disablement signal includes sufficient current and/or voltage to disable or "blow" the fuse. A disabled fuse prevents traversal of the electrical path or circuit by the status signal, thereby indicating that the disposable item has prior use and is typically non-sterile. Accordingly, if the microprocessor does not detect the status signal returned from the fuse at step 72 (e.g., indicating prior use or non-sterility of the disposable item), the microprocessor disables medical device operation and enables various audio and/or visual indicators (e.g., beep, flashing red indicator, etc.) at step 88. Thus, a disabled item fuse basically prevents reuse of that item with the medical device since the microprocessor does not detect the initial status signal and consequently disables device operation.

Once the disablement signal is transmitted at step 74, the microprocessor subsequently transmits the status signal to the fuse at step 76 and senses the return of that signal from the fuse at step 78. This is performed to ensure that the fuse is disabled and to prevent operation of the medical device when a conductive element (e.g., coin) has been disposed on the disposable item to falsely indicate an enabled fuse. In other words, this fuse status check prevents use of prior utilized items employing a conductive element to circumvent the prior use or sterility determination. If the fuse is enabled after transmission of the disablement signal as determined at step 78 (e.g., the status signal is sensed by the microprocessor), the item is considered to include a conductive element and the microprocessor disables medical device operation and enables audio and/or visual indicators at step 88 as described above.

When the fuse is disabled after transmission of the disablement signal as determined at step 78, a proper sterile item is present and the microprocessor enables medical device operation. Control of device operation may be accomplished, in the case of an independent processor, by controlling power or other signals to the medical device controller and/or components. Alternatively, when the apparatus employs the medical device controller, the controller may selectively perform device functions in response to the fuse status. During device operation, the microprocessor repeatedly checks the status of the fuse by transmitting and sensing the status signal at steps 84 and 86. The medical device continues to operate until the device is powered down or reset as determined at step 82, or until a returned status signal is detected at step 86 indicating an enabled fuse.

When a returned status signal is detected at step 86, this typically indicates that the medical device has received either a new sterile disposable item with an enabled fuse or a prior used item with a conductive element. In order to determine the nature of the received item, the microprocessor transmits the disablement signal and checks the status of the fuse at steps 74, 76 and 78 as described above. If the microprocessor detects a returned status signal at step 78 after transmission of the disablement signal, this is considered to indicate the presence of a non-sterile item with a conductive element and the microprocessor disables medical device operation and enables audio and/or visual indicators at step 88 as described above. When the microprocessor does not detect a returned status signal at step 78 after transmission of the disablement signal, this indicates the presence of a new sterile disposable item with a properly disabled fuse and the microprocessor enables device operation, repeatedly checks the fuse status and controls device operation accordingly as described above.

Figure 4:
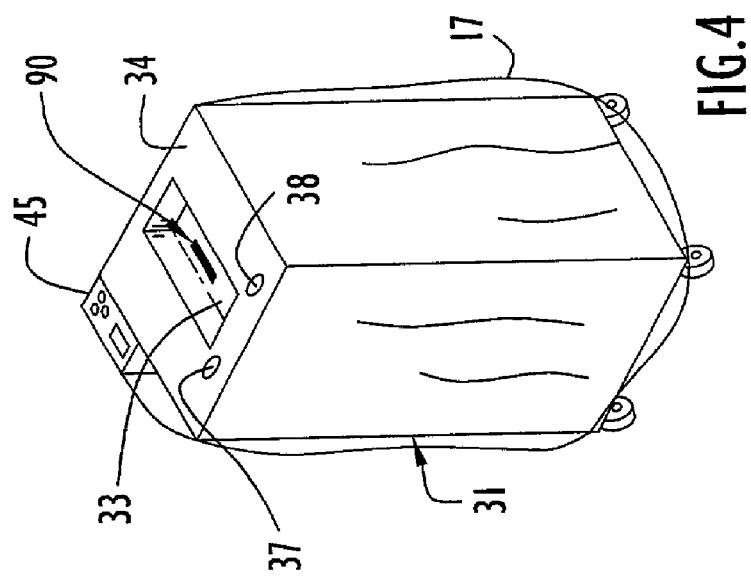
FIG. 4 is a perspective view of exemplary medical equipment in the form of a thermal treatment system employing the apparatus of the present invention to determine prior use or sterility of a disposable surgical drape.

The apparatus of the present invention may be utilized with any types of medical devices employing disposable sterile items. An alternative medical device employing the present invention may include a thermal treatment system and corresponding disposable surgical drape as illustrated in FIG. 4. Specifically, the system includes a cabinet or housing 31, a wiring housing 45 attached to the cabinet and a warming basin 33 recessed into a cabinet top surface 34. Basin 33 may be of any shape, however, by way of example only, the basin is illustrated as being substantially rectangular. A heater power switch 37 and a temperature controller/indicator 38 are provided on top surface 34 toward the cabinet front wall with the warming basin residing between the power switch and controller. Wiring housing 45 is attached to the cabinet side wall that is closest to heater power switch 37 and facilitates system connections as described below. A heater is disposed on the underside of the basin to heat the basin and the sterile medium contained therein. The heater is controlled by controller 38 in accordance with an entered desired temperature and temperatures measured by a temperature sensor. A sterile drape 17, preferably transparent, is typically disposed over the top and sides of cabinet 31 and made to conform to the side wall and bottom of basin 33. Power switch 37 and controller 38 are disposed on top surface 34 of system cabinet 31 and are adjustable manually through drape 17. The portion of drape 17 disposed in basin 33 serves as a sterile container or receptacle for sterile liquid placed therein to be heated. The drape is designed to be disposable after a single use and is provided presterilized and prepackaged in a manner to preserve its sterile state during storage.

Figure 5:
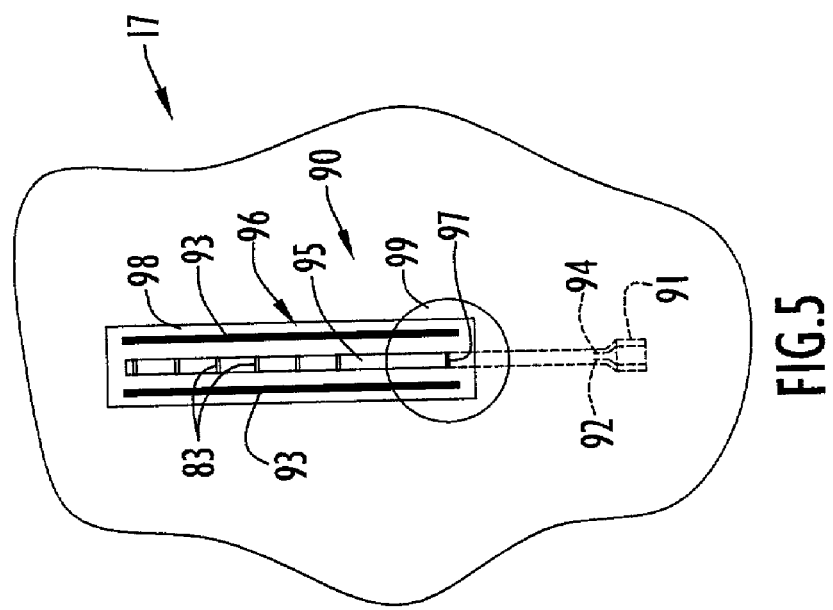
FIG. 5 is a view in perspective of the surgical drape of FIG. 4.

The drape is typically positioned over the thermal treatment system with a portion of the drape disposed in a basin to form a drape receptacle as described above. The drape forms a sterile field above the basin to maintain sterility of the sterile medium. The drape may be a basic drape to contain the medium or, alternatively, include special features to enhance system operation. One such feature includes detecting the presence of liquid and/or leaks within the drape container to maintain drape integrity and sterility of the sterile medium. An exemplary drape 17 including a sensing device for this purpose is illustrated in FIG. 5. Specifically, drape 17 includes a sensing device 90 to detect the presence of liquid and leaks within a drape container. Sensing device 90 is in the form of a pair of electrodes 92, 94 that are affixed to a generally rectangular strip 95 disposed on an intermediate portion of the drape sterile surface. The electrodes are disposed on the electrode strip toward respective strip longer dimensioned edges and extend substantially in parallel. The electrode strip is enclosed within a pouch 96 to secure the electrodes to the drape and to protect the electrodes from sharp objects that maybe disposed within the basin. The pouch is formed from a substantially rectangular segment or flap 98 that is attached (e.g., welded) to the drape sterile surface and sealed by seams 93, each formed toward and extending along a respective flap longer dimensioned edge. In order to enable the liquid in the drape container to contact the electrodes and facilitate current flow between those electrodes as described below, flap 98 includes a series of slots 83. The slots are defined in the flap between seams 93 and are spaced from each other in a direction of the flap longer dimension. The slots are generally rectangular and extend substantially perpendicular to electrodes 92, 94. Each slot includes a longer dimension substantially similar to the width of strip 95 and encompasses portions of each electrode 92, 94 to facilitate enhanced exposure of the electrodes to liquid within the drape container. Alternatively, the flap may include any quantity of slots or openings of any shape or size and disposed at any locations in any desired fashion to facilitate contact between the electrodes and liquid within the drape container.

The distal ends of the electrodes are attached to a plug or connector 91 that interfaces detection circuitry within the thermal treatment system. The plug includes electrode traces disposed on a plug top surface. The distal portions of strip 95 and electrodes 92, 94 pass through the drape from the sterile to the non-sterile drape sides via an opening or slit 97 defined in the drape at a location slightly offset from a drape central portion. A substantially circular segment or patch 99 is attached to the sterile drape surface to seal opening 97. The patch basically encompasses opening 97 and effectively seals that opening to prevent escape of liquid from, and maintain sterility of, the drape container. Flap 98 and patch 99 are preferably constructed of drape materials, however, the flap and patch may be constructed of any suitable materials, may be of any shape or size, and may be disposed on the drape at any suitable locations via any conventional or other techniques.

Sensing device 90 detects the presence of liquid and leaks within the drape container in response to placement of drape 17 over the thermal treatment system. In particular, current flow between the electrodes is initiated in response to the electrodes contacting liquid. Further, the presence of a leak within the drape container enables current to flow between the electrodes and ground (e.g., the basin beneath the drape). The current flow from each of these conditions causes a respective change in voltage that is detected by detection circuitry within the thermal treatment system. The magnitude of the voltage change is utilized by the detection circuitry to detect the presence of solution and/or leaks within the drape container and to control system operation in accordance with the detected conditions. Wiring housing 45 (FIG. 4) receives signals from the electrodes and includes wiring to transfer signals between that housing and the detection circuitry. The housing further includes indicators in the form of light emitting diodes to indicate drape container conditions. The detection circuitry determines the drape container conditions based on the electrode signals and controls system operation accordingly. In addition, the detection circuitry selectively illuminates the diodes to indicate the particular determined drape container conditions. For further examples of the operation and structure of these types of thermal treatment systems and drapes, reference is made to U.S. Pat. No. 5,524,643 (Faries, Jr. et al) and 5,653,938 (Faries, Jr. et al) and U.S. patent application Ser. No. 09/983,021, entitled "Medical Solution Thermal Treatment System and Method of Controlling System Operation in Accordance with Detection of Solution and Leaks in Surgical Drape Containers" and filed Oct. 22, 2001, the disclosures of which are incorporated herein by reference in their entireties.

The thermal treatment system and drape may employ the apparatus of the present invention in substantially the same manner described above. Basically, the drape includes the fuse and corresponding wire segments and contacts (e.g., or plug and/or connector arrangement) disposed at any suitable locations, while the thermal treatment system includes the microprocessor and corresponding wire segments and contacts (e.g., or plug and/or connector arrangement) disposed thereon or therein in any desired fashion. The microprocessor may be an independent processor for the apparatus or be implemented by the thermal treatment system controller. The microprocessor determines drape prior use or sterility and controls system operation accordingly in substantially the same manner described above for FIGS. 2–3, where the system corresponds to medical device 10 and the drape corresponds to disposable item 20.

Figure 6:
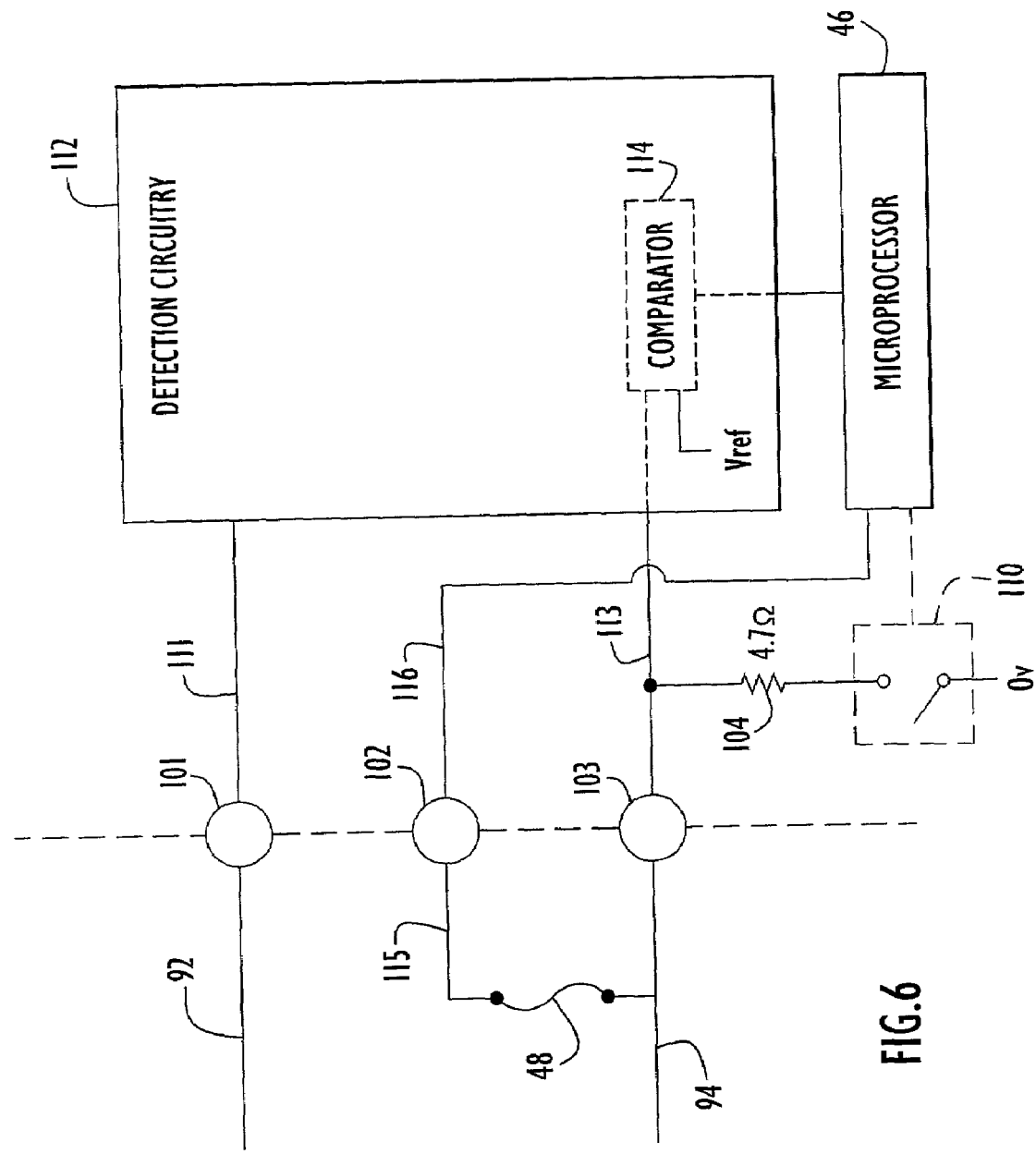
FIG. 6 is an electrical schematic diagram of an exemplary apparatus of the present invention for use with the equipment of FIG. 4 to determine prior use or sterility of a disposable surgical drape.

Alternatively, the present invention apparatus maybe coupled to the thermal treatment system detection circuitry to determine drape prior use or sterility as illustrated in FIG. 6. Specifically, the apparatus is similar to the apparatus described above for FIG. 2 and includes microprocessor 46 and fuse 48. The present invention preferably employs an independent microprocessor, however, a microprocessor or controller of the thermal treatment system may be utilized. The fuse is disposed on the drape and coupled to electrode 94, while the microprocessor is typically disposed within the thermal treatment system and coupled to detection circuitry 112. The detection circuitry receives signals from the electrodes to determine the presence of solution and leaks within the drape container as described above. Electrodes 92, 94 on the drape are respectively connected to pins 101, 103 of a connector coupling the electrodes to the thermal treatment system. Pins 101, 103 basically provide signals from the electrodes to the detection circuitry via conductors or wiring 111, 113, respectively. The connector further includes a pin 102 coupled to microprocessor 46 via wiring 116 and to fuse 48 via wiring 115 to enable the microprocessor to transmit signals to the fuse. The fuse is disposed between pin 102 and electrode 94 on the drape, while additional circuitry is coupled to wiring 113 and disposed between pin 103 and detection circuitry 112. The additional circuitry includes a resistor 104 (e.g., 4.7 Ohms) disposed in series with a switch 110 controlled by microprocessor 46. The switch and resistor are disposed between wiring 113 and ground and facilitate determination of the fuse status as described below. The microprocessor basically closes switch 110, thereby forming an electrical path from pin 102 to ground (e.g., from pin 102 and through fuse 48, electrode 94, pin 103, resistor 104 and switch 110). Electrode 94 is coupled (e.g., via pin 103 and wiring 113) to a comparator 114 within the detection circuitry. The comparator is utilized by the detection circuitry to interpret the electrode signals, and is coupled to the microprocessor. The comparator compares the signal from electrode 94 to a reference voltage and produces an output signal utilized by the microprocessor to detect the presence of the status signal through the fuse.

Operation of the apparatus is substantially similar to that described above for FIG. 3, except that the microprocessor controls switch 110 and receives the comparator output to determine the presence of status signals. Initially, a drape with fuse 48 is disposed on the thermal treatment system. The electrodes are coupled via plug 91 to the system circuitry as described above. The microprocessor initializes, closes switch 110 and transmits a status signal (e.g., 5V DC) to pin 102. The signal traverses the pin and fuse, and places electrode at a potential of approximately 5V DC. The electrode is coupled to comparator 114 that compares the electrode potential to a reference voltage and provides an output signal to microprocessor 46. The microprocessor analyzes the comparator output signal to determine the presence of a returned status signal from the fuse. In other words, when the fuse is enabled, the microprocessor detects a return signal based on the comparator output. If the microprocessor does not sense the return signal, the fuse is disabled indicating a prior used or non-sterile drape and device operation is disabled. If the return signal is present, the fuse is enabled and the microprocessor waits a predetermined time interval (e.g., one second) and transmits the disablement signal (e.g., including sufficient current and/or voltage) to disable or "blow" the fuse. The microprocessor subsequently transmits the status signal and detects the presence of the return signal as described above to determine disablement of the fuse. If the return signal is detected after transmission of the disablement signal, this is considered to indicate the presence of a non-sterile drape employing a conductive member (e.g., coin) in place of the fuse and the microprocessor disables system operation. Control of device operation maybe accomplished, in the case of an independent microprocessor, by controlling power or other signals to the system controller and/or components. Alternatively, when the apparatus employs the system controller, the controller may selectively perform system functions in response to the fuse status. If a return signal is not detected, the microprocessor opens the switch and enables system operation to treat sterile medium and detect the presence of liquid and leaks as described above.

The microprocessor repeatedly checks the status of the fuse by closing the switch, transmitting the status signal and examining the return signal as described above. If no return signal is detected, system operation continues until power down or a condition (e.g., leak or no solution) is detected. When a condition (e.g., leak) is detected, the system is powered down (e.g., reset), where a new drape with a fuse is typically required to be placed on the system in order to proceed. When a return signal is detected during operation, this typically indicates replacement of the drape with either a new sterile drape and corresponding fuse or a prior used drape employing a conductive member. The microprocessor attempts to disable the fuse as described above to determine the particular event. When the fuse is not disabled via transmission of the disablement signal, a conductive member is considered to be employed with a non-sterile drape and the microprocessor disables system operation as described above. If the microprocessor disables the fuse via transmission of the disablement signal, anew drape has been utilized and the microprocessor enables device operation, repeatedly checks the fuse status and controls system operation accordingly as described above. Thus, the apparatus ensures operation of the medical device with a disposable sterile item.

It is to be understood that the thermal treatment system described above may have various configurations. For example, the thermal treatment system maybe configured to cool and/or congeal the medium to produce cooled liquid or surgical slush. In this instance, the heater may be replaced by refrigeration devices, while the prior use or sterility of the drape may be determined in substantially the same manners described above for FIGS. 2–3 and 6. Further, the thermal treatment system may include a plurality of basins warming and/or cooling a sterile medium. In particular, a plural basin drape (e.g., a drape capable of forming a drape receptacle for each thermal treatment system basin) may include a fuse and corresponding wiring similar to the arrangement illustrated in FIG. 2 to indicate prior use or sterility of the entire drape in substantially the same manner described above. Moreover, the plural basin drape may include a plurality of fuses and corresponding wiring each similar to the arrangement illustrated in FIG. 2 and associated with an individual drape receptacle, where the microprocessor is coupled to and transmits and receives signals from the plural fuses to determine prior use or sterility of the individual drape receptacles in substantially the same manner described above. Alternatively, the plural basin drape may include a plurality of sensing devices each associated with a drape receptacle, where a fuse and corresponding circuitry may be coupled to a sensing device similar to the arrangement illustrated in FIG. 6 to indicate prior use or sterility of the entire drape in substantially the same manner described above. In addition, the plural basin drape may include a plurality of sensing devices, fuses and corresponding circuitry with each fuse and corresponding circuitry coupled to a sensing device similar to the arrangement illustrated in FIG. 6, where the microprocessor is coupled to and transmits and receives signals from the plural fuses to determine prior use or sterility of the individual drape receptacles in substantially the same manner described above. The individual drape receptacle determinations may be combined by the microprocessor or other circuitry in any fashion to achieve an overall prior use or sterility determination for the plural basin drape. Examples of cooling and/or plural basin systems and drapes are disclosed in several Faries, Jr. et al. patents (e.g., U.S. Pat. Nos. 5,333,326; 5,429,801; 5,522,095; 5,524,643; 5,615,423; 5,653,938; 5,816,252; 5,862,672; 5,857,467; 5,879,621; 6,091,058; and 6,255,627), the disclosures of which are incorporated herein by reference in their entireties.

It will be appreciated that the embodiments described above and illustrated in the drawings represent only a few of the many ways of implementing a method and apparatus for ensuring sterility of disposable medical items used with medical equipment.

The present invention maybe employed with any types of medical or other devices to prevent reuse of an item. The medical device may be any device handling a sterile object, while the disposable item may be any item requiring sterility or maintaining sterility for the sterile object. The present invention may be utilized to prevent reuse of disposable or non-disposable items (e.g., an unsterilized non-disposable item, where the non-disposable item includes a device indicating sterilization of that item after a prior use).

The warming device may be of any shape or size, may be positioned at any desired locations in any orientation, and may heat any types of medical or other fluids. The device housing may be of any shape or size and may be constructed of any suitable materials. The housing materials are preferably transparent to enable viewing of the fluid and any conditions within the device (e.g., contamination, air bubbles, etc.), but may have any degree of transparency (e.g., transparent, translucent, opaque, etc.). The controller may be disposed at any suitable location on or within the housing. The housing interior may include any suitable configuration to partially or completely receive any quantity of controllers, base plates, heater plates, IV tubing cassettes or other device components. For example, the housing may be configured for receiving a plurality of tubing cassettes in order to heat fluid within plural separate IV fluid lines. The device components may be arranged in any fashion within the housing.

The base plate may be of any quantity, shape or size, may include any suitable configuration and may be constructed of any suitable materials. The base plate is preferably transparent to enable viewing of the fluid as described above, but may have any degree of transparency (e.g., transparent, translucent, opaque, etc.). The base plate may be secured at any suitable location on or within the housing. The heater plate may be of any quantity, shape or size, and may be constructed of any suitable thermally conductive materials. The heater plate may include any suitable configuration for being received and retained by the base plate and for heating the tubing cassette. The heater plate may include any quantity of any type of conventional or other heating element secured to the plate at any desired locations via any securing techniques (e.g., bracket, adhesives, etc.).

The tubing cassette may be of any quantity, shape or size and may be constructed of any suitable materials. The cassette may include any suitable configuration for being received and retained by the base plate. The inlet and outlet tubing portions of the cassette may include any suitable connector for securing those portions to any desired sections of an IV line. The outlet portion may alternatively direct heated fluid from the cassette to any desired location (e.g., an infusion or other site, a storage container, etc.). The cassette may include any type of tubing or other materials suitable to define a flow path for fluid. The cassette may include any quantity of tubing sections arranged in any desired manner (e.g., concentric, serpentine, zig-zag, linear, spiral, etc.) to provide sufficient residence time for fluid within the device, wherein fluid flow directions within the sections may be arranged in any desired pattern or fashion. The cassette may include any quantity of concentric tubing sections, while the serpentine section may include any configuration (e.g., serpentine, circular, linear, spiral, etc.) that reverses fluid flow within the cassette. The serpentine section may be disposed at any location within the fluid flow path. The warming device may accommodate any quantity of cassettes, while the cassette may include any quantity of tubing section layers (e.g., any quantity of tubing sections on any quantity of planes (e.g., each stacked above or adjacent the other, etc.)). The cassette may include any suitable structures to form the fluid flow path (e.g., tubing, sealed channels, pools, chambers, etc.). The inlet and outlet portions may be used in any fashion to enable fluid to flow into and out of the cassette. The cassette backing may be of any quantity, shape or size, may receive the cassette at any suitable locations, and may be constructed of any suitable materials. The backing may include any quantity of tabs of any shape or size and disposed at any suitable locations. The tabs may be constructed of any suitable materials.

The housing cover may be of any quantity, shape or size, and may be constructed of any suitable materials. The cover is preferably transparent to enable viewing of the fluid as described above, but may have any degree of transparency (e.g., transparent, translucent, opaque, etc.). The cover may be secured to the housing or base plate in any manner, and may include any quantity of any type of handle or other structure of any shape or size and disposed at any suitable location to facilitate manipulation of the cover. The cover may include any quantity of any type of conventional or other heating device (e.g., heating pad, acrylic heater, coils, etc.).

The warming device controller may be implemented by any quantity of any conventional or other microprocessor, controller or circuitry. The controller may be disposed at any suitable location on or within the housing or separate from the device (e.g., wireless or other communication link to components, etc.). The controller may include any quantity of any type of display (e.g., LED, LCD, etc.) or indicators (e.g., visual, audio, speech synthesis, etc.) disposed at any suitable locations to convey any desired information or conditions to an operator (e.g., desired temperatures, measured temperatures, improper placement of cassette within device, etc.). The controller may include any quantity of any type of input devices (e.g., buttons, keys, voice recognition, etc.) to receive information. The controller may further serve to control the safety apparatus of the present invention.

The fluid temperature may be predetermined or entered by a user, where the device typically heats fluid to temperatures in the approximate range of 60° F.–160° F. However, the device may be utilized to heat and/or cool fluid (e.g., by employing cooling or refrigeration devices instead of or in conjunction with the heating elements) to any desired temperature or temperature range.

The warming, cooling and plural basin systems and their corresponding cabinets, assemblies or housings may be of any shape or size and may be constructed of any suitable materials. The plural basin system may include any quantity of heating and/or cooling basins in any combinations. The basins of the systems may be of any shape or size, may be constructed of any suitable thermal conducting materials (e.g., stainless steel) and may be disposed at any suitable locations on or within the housings. The systems may include any conventional or other heating and/or refrigeration units to thermally treat the sterile medium or other substance to any desired temperature. The heating unit may include any conventional or other heating device and components to control heating of a basin to any desired temperature (e.g., preferably to temperatures near (e.g., above, at or below) body temperature, such as temperatures in the approximate range of 60° F.–160° F.). The heater may be of any quantity (e.g., at least one), shape or size, and may include any configuration (e.g., strips, bars, segments, etc.) that covers the entirety or any portion of a basin. The heater may be attached to a basin via any conventional or other fastening techniques (e.g., any type of adhesives, brackets, etc.). In addition, the heater may be implemented by any conventional or other type of heater or heating element (e.g., heating coils, etc.) that may be disposed on or proximate a basin at any suitable locations.

The cooling unit may include any conventional or other cooling or refrigeration device and components to control cooling of a basin to any desired temperature (e.g., preferably to temperatures near or below the freezing temperature of the sterile liquid or medium, such as temperatures in the approximate range of −32° F. to 32° F.). The various power switches and controllers of the systems may be implemented by any conventional or other power and control devices and may be disposed on the systems at any suitable locations.

The temperature sensor maybe implemented by any conventional or other temperature sensing device (e.g., infrared, RTD, etc.) and may be disposed at any location on or proximate a basin or within the systems. The basins of the systems may be disposed in any arrangement or at any suitable locations on the systems. The systems may thermally treat (e.g., heat or cool) any type of medium or liquid, while a cooling basin may further include any type of conventional or other dislodgement mechanism, such as those described in the aforementioned Faries, Jr. et al patents.

The wiring housing may be of any quantity, shape or size, may be constructed of any suitable materials, and may be disposed at any suitable locations on the systems. The wiring housing and/or systems may include any suitable conductors or other medium (e.g., wireless, fiberoptics, etc.) to transfer signals between system components. The wiring housing may include any quantity of any type of indicator (e.g., audio, speech synthesis, LED, display screen with text or images, etc.) to indicate the drape container status. The indicator may be disposed on the wiring housing or systems at any suitable locations. The diodes may be of any quantity or color, may be disposed at any suitable locations on the wiring housing or systems and may be illuminated in any desired fashion or pattern (e.g., flashing, continuous illumination, etc.). A drape container or other condition may be associated with any quantity of any diodes of any color (e.g., the same or different colors in any desired combinations).

The drapes employed with the heating, cooling and plural basin systems maybe of any size or shape, and may be constructed of any suitable materials. The drapes are preferably transparent or translucent to facilitate manipulation of controls through the drape, however, these drapes may have any degree of transparency (e.g., including opaque). The drapes may be manipulated in any fashion with any portions of the drapes serving as a drape receptacle within a corresponding basin. The drapes maybe of sufficient size to accommodate and form drape receptacles within any quantity of thermal treatment system basins.

The sensing device may include any quantity of electrodes or electrode strips disposed at any suitable locations on a drape. The electrodes may be constructed of any suitable conductive materials. The electrode strip may be of any shape or size, and may be constructed of any suitable materials. The electrodes may be fastened to the strip at any suitable locations via any conventional or other fastening techniques. The pouch may be of any quantity, shape or size, may be constructed of any suitable materials, may contain any portions of the electrodes or electrode strip and maybe fastened to the drape at any suitable locations via any conventional or other fastening techniques. The flap may be of any quantity, shape or size, may be attached to the drape at any suitable locations via any conventional or other fastening techniques to form the pouch and may be constructed of any suitable materials. The seams may be disposed on the flap at any suitable locations to attach the flap to the drape to form the pouch. The flap may include any quantity of openings or slots of any shape or size disposed in any suitable locations on the flap or pouch and arranged in any fashion to enable liquid within the drape container to contact the electrodes. Alternatively, the sensing device or electrode strip maybe attached to the drape (i.e., without the pouch) via the patch or any other securing mechanisms (e.g., adhesives, welding, etc.) to sense drape container conditions.

The drape opening may be of any quantity, shape or size and may be defined in the drape at any suitable locations. The patch may be of any quantity, shape or size, may be constructed of any suitable materials and may be disposed at any suitable locations on the drape. The drape may include any quantity of openings and corresponding patches disposed on or attached to either or both of the sterile and non-sterile drape surfaces. The drape may include any quantity of sensing devices for a corresponding basin where the sensing device signals may be combined in any fashion (e.g., at least one device detecting liquid, combined logically (e.g., AND, OR, etc.), etc.) to determine occurrence of drape container conditions (e.g., solution or leaks present). The sensing device plug may be implemented by any conventional or other plug or connector where the electrode traces may be disposed at any locations on the plug. Alternatively, the electrode strip or other objects may traverse a drape peripheral or other edge (e.g., without being disposed through the drape) to extend between the sterile and non-sterile drape surfaces.

The temperature controller may be implemented by any conventional or other temperature controller and include any desired devices for entering a temperature (e.g., buttons, keypad, etc.). The temperature controller may further serve to control the safety apparatus of the present invention. The basin power switches of the systems may be implemented by any conventional or other switching device.

The drape may facilitate placement of any types of objects (e.g., conductors, tubes or other fluid passages, various communication medium, etc.) through or around the drape in any manner (e.g., traverse any drape opening or drape edge, etc.) to enable communication or passage between the sterile and non-sterile sides of the drape without compromising the sterile field. Further, the electrodes or other communication medium may be connected to various sensors or any other types of measuring, analytical and/or control devices to measure, determine and/or indicate any types of conditions and/or control system operation in any desired fashion in response thereto.

The safety apparatus of the present invention may employ an independent processor or a processor of the medical device to determine prior use or sterility of an item. The processor may be implemented by any quantity of any conventional or other processors (e.g., microprocessors, controllers, etc.) or circuitry performing the functions described herein. The power supply may be implemented by any quantity of any conventional or other power supply and may convert any power signals to appropriate signals for the microprocessor. The input power signals to the power supply and output power signals to the microprocessor may be of any desired types and/or magnitudes (e.g., any voltage or current, AC, DC, etc.). The processor may control medical device operation in any manner in response to the sterility determination (e.g., controlling power or other signals to the device or device components, directly controlling device operation, etc.). The software and/or control functions of the processor may be developed by one of ordinary skill in the computer arts based on the functions described herein and the flow chart illustrated in the drawing. The algorithms and/or procedures described herein and illustrated in the drawings may be modified in any manner accomplishing the described functions. The various functions and/or software of the processor may be distributed in any fashion among any quantity of processors, circuitry or hardware and/or software units or modules. The medical devices or the present invention apparatus may include any types of indicators to indicate a prior used or non-sterile item (e.g., audio, visual, LEDs or other visual indicators of various colors or flashing at any desired frequency, speech synthesis, alarm sound either continuous or beeping at any desired frequency, etc.).

The wiring and wire segments of the medical devices and disposable items may be of any quantity, size or shape, may be disposed at any desired locations and may be constructed of any suitable conductive materials. The wiring and wire segments may alternatively be implemented by any suitable medium for a wired or wireless embodiment (e.g., hardwired, optical, radio signals, audio, etc.). The wire segments and wiring may be arranged in any fashion and transport signals in any manner to, from or between components. The contacts maybe of any quantity, shape or size, maybe constructed of or include any desired conductive materials and may be disposed at any desired locations to couple the wire segments. Alternatively, the wire segments may include any type of coupling arrangement (e.g., plug/connector, contacts, wireless connection, mechanical connections, optical connections, etc.) to form the electrical or other path (e.g., optical, radio or wireless, audio, etc.).

The fuse may be implemented by any type of electrical, mechanical or other device (e.g., transistor, fuse, switch, relay, optical device, audio device, electromechanical device, etc.) selectively controlled to disrupt or disable the electrical or other path (e.g., optical, wired, radio or wireless, audio, etc.). Alternatively, the fuse may be implemented by any device accessible by the processor and including plural states to indicate sterility or prior use of the item (e.g., memory, optical indicators (e.g., LEDs or other devices with on/off states), etc.). The fuse may be of any quantity, shape or size, may include any current and/or voltage thresholds and may be accompanied by any additional circuitry (e.g., resistors, capacitors, inductors, switches, transistors, etc.) for a particular application. The fuse maybe constructed of any materials (e.g., glass fuse, thin painted metallic line, etc.). The status and disablement signals may be of any quantity or magnitude sufficient to test the fuse status or disable the fuse (e.g, these signals may be of any voltage or current types or levels (e.g., digital, analog, AC, DC, volts, amps, any fractions of volts or amps, etc.)). The microprocessor may transmit the status and disablement signals in any fashion and in response to any desired conditions or at any desired time intervals (e.g., the status signals may be sent periodically, the disablement signal may be transmitted at any desired time interval after transmission of a status signal, etc.).

The detection circuitry may include any conventional components (e.g., processor, logic gates, comparators, etc.) arranged in any fashion to detect solution and leaks. The present invention safety apparatus may be coupled to any portion of the detection or other medical device circuitry to detect the presence of the status signal. The comparator may be implemented by any conventional or other components or circuitry to compare or detect the status signal and may include any reference potential to indicate to the processor the presence of a status signal. The wiring between the electrodes, connector and detection circuitry may be of any quantity, shape or size, may be disposed in any fashion and may be constructed of any conductive materials. The controlled switch may be implemented by any conventional or other switching device (e.g., switch, transistor, mechanical device, relay, etc.) and be responsive to any control signal from the processor or other device (e.g., circuitry, etc.). The resistor may include any suitable resistance to create the electrical path from the pin to ground through the switch.

The plural basin drape may employ the present invention safety apparatus to indicate prior use or sterility of the entire drape, or may include a plurality of safety apparatus each associated with an individual drape receptacle to determine prior use or sterility of the individual drape receptacles. Alternatively, the plural basin drape may include a plurality of sensing devices each associated with a drape receptacle, where a safety apparatus may be coupled to a sensing device to indicate prior use or sterility of the entire drape. In addition, the plural basin drape may include a plurality of sensing devices and a plurality of safety apparatus with each safety apparatus coupled to a sensing device, where the microprocessor is coupled to and transmits and receives signals from the plural safety apparatus to determine prior use or sterility of the individual drape receptacles. The individual drape receptacle determinations may be combined by the processor or other circuitry in any fashion to achieve an overall prior use or sterility determination for the plural basin drape.

The warming device, drape or other disposable items may include any quantity of safety apparatus, where the apparatus results may be combined in any fashion to produce a prior use or sterility determination. Further, the present invention may employ any type of device or circuitry within the disposable item capable of indicating a state of the item (e.g., fuse, memory, another processor, switch, etc.) and accessible by a medical device processor or circuitry to ascertain and/or alter the state to determine and/or indicate prior use of the item. The various components (e.g., processors, circuitry, wiring, fuses, contacts, plugs and/or connectors, etc.) of the present invention safety apparatus may be distributed between and disposed on or within the medical device and/or disposable item in any desired fashion and/or at any suitable locations.

It is to be understood that the terms "lead", "return", "horizontal", "vertical", "length", "width", "upper", "lower", "side", "front", "rear", "top", "bottom" and the like are used herein merely to describe points of reference and do not limit the present invention to any particular configuration or orientation.

From the foregoing description, it will be appreciated that the invention makes available a novel method and apparatus for ensuring sterility of disposable items used with medical equipment, wherein a medical device accesses circuitry within a disposable medical item to determine prior use or sterility of that item and control device operation accordingly.

Having described preferred embodiments of a new and improved method and apparatus for ensuring sterility of disposable items used with medical equipment, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An apparatus to determine prior use of a disposable item utilized with a medical device comprising:
    a status device including a plurality of states and secured to said disposable item, wherein the state of said status device indicates a prior use of said disposable item; and
    a processor coupled to said medical device and to said status device to determine said prior use of said disposable item based on said status device state and to facilitate control of medical device operation in accordance with said prior use determination, wherein said status device includes a conducting element disposed within an electrical path extending between said status device and said processor with a first state of said conducting element enabling said electrical path and indicating an unused disposable item and a second state of said conducting element disabling said electrical path and indicating prior use of that item, and wherein said processor includes:
        a status module to transmit a status signal over said electrical path to said conducting element and to detect a return signal on said electrical path from said conducting element to determine said state of said conducting element and ascertain said prior use of said disposable item;
        an element module to disable said electrical path by controlling said conducting element to enter said second state in response to detection of said return signal by said status module, thereby indicating use of said disposable item; and
        a verification module to re-transmit said status signal over said electrical path to said conducting element in response to said disablement by said element module and to verify placement of the conducting element in said second state by said element module, wherein said verification module determines the presence of an unused disposable item with said conducting element in said second state in response to detection of the absence of said return signal and determines the presence of a used disposable item utilizing a conductive member with said conducting element in said second state in response to detection of said return signal.

2. The apparatus of claim 1, further including:
    item wire segments extending from said conducting element and including item coupling members attached thereto; and
    device wire segments extending from said processor and including device coupling members attached thereto;
    wherein said disposable item is received by said medical device with said item coupling members engaging said device coupling members to form said electrical path.

3. The apparatus of claim 2, wherein said item and device coupling members include contacts.

4. The apparatus of claim 2, wherein said item and device coupling members include plugs and corresponding connectors.

5. The apparatus of claim 1, wherein said conducting element is a fuse.

6. The apparatus of claim 1, wherein said element module includes:
    a transmission module to place said conducting element in said second state by transmitting a disablement signal of sufficient magnitude to disable said conducting element.

7. The apparatus of claim 1, wherein said processor further includes:
    a control module to control medical device operation in response to said prior use determination of said disposable item.

8. The apparatus of claim 7, wherein said control module includes:
    a device enablement module to enable medical device operation in response to an unused disposable item as indicated by said detection of the absence of said return signal by said verification module; and
    a device disablement module to disable operation of said medical device in response to a used disposable item as indicated by detection of the absence of said return signal by said status module or by said detection of said return signal by said verification module.

9. The apparatus of claim 8, wherein said processor further includes:
    an operation status module to transmit a status signal over said electrical path to said conducting element periodically during medical device operation enabled by said device enablement module and to detect a return signal on said electrical path from said conducting element to determine said state of said conducting element, wherein detection of said return signal indicates insertion of a new disposable item;
    an operation element module to disable said electrical path by controlling said conducting element of said new disposable item to enter said second state in response to detection of said return signal by said operation status module, thereby indicating use of said new disposable item;
    an operation verification module to re-transmit said status signal over said electrical path to said conducting element of said new disposable item in response to said disablement by said operation element module and to detect the absence of a return signal from said conducting element to verify placement of that conducting element in said second state by said operation element module, wherein said detection of the absence of said return signal by said operation verification module indicates an unused disposable item with said conducting element in said second state and said detection of said return signal by said operation verification module indicates a used disposable item utilizing a conductive member with said conducting element in said second state; and an operation disablement module to disable operation of said medical device in response to a used disposable item as indicated by said detection of said return signal by said operation verification module.

10. A medical device determining prior use of a disposable item utilized with that device to control device operation, wherein said disposable item includes a status device including a plurality of states and secured to said disposable item, and wherein the state of said status device indicates a prior use of said disposable item, said medical device comprising:

a housing to receive and treat said disposable item; and a processor coupled to said status device to determine said prior use of said disposable item based on said status device state and to facilitate control of medical device operation in accordance with said prior use determination, wherein said status device includes a conducting element disposed within an electrical path extending between said status device and said processor with a first state of said conducting element enabling said electrical path and indicating an unused disposable item and a second state of said conducting element disabling said electrical path and indicating prior use of that item, and wherein said processor includes:

a status module to transmit a status signal over said electrical path to said conducting element and to detect a return signal on said electrical path from said conducting element to determine said state of said conducting element and ascertain said prior use of said disposable item;

an element module to disable said electrical path by controlling said conducting element to enter said second state in response to detection of said return signal by said status module, thereby indicating use of said disposable item; and a verification module to re-transmit said status signal over said electrical path to said conducting element in response to said disablement by said element module and to verify placement of the conducting element in said second state by said element module, wherein said verification module determines the presence of an unused disposable item with said conducting element in said second state in response to detection of the absence of said return signal and determines the presence of a used disposable item utilizing a conductive member with said conducting element in said second state in response to detection of said return signal.

11. The device of claim 10, wherein said disposable item includes item wire segments extending from said conducting element and including item coupling members attached thereto, and said medical device further includes:

device wire segments extending from said processor and including device coupling members attached thereto;

wherein said disposable item is received by said medical device with said item coupling members engaging said device coupling members to form said electrical path.

12. The device of claim 10, wherein said conducting element is a fuse and said element module includes:

a transmission module to place said conducting element in said second state by transmitting a disablement signal of sufficient magnitude to disable said conducting element.

13. The device of claim 10, wherein said processor further includes:

a control module to control medical device operation in response to said prior use determination of said disposable item.

14. The device of claim 13, wherein said control module includes:

a device enablement module to enable medical device operation in response to an unused disposable item as indicated by said detection of the absence of said return signal by said verification module; and a device disablement module to disable operation of said medical device in response to a used disposable item as indicated by detection of the absence of said return signal by said status module or by said detection of said return signal by said verification module.

15. The device of claim 14, wherein said processor further includes:

an operation status module to transmit a status signal over said electrical path to said conducting element periodically during medical device operation enabled by said device enablement module and to detect a return signal on said electrical path from said conducting element to determine said state of said conducting element, wherein detection of said return signal indicates insertion of a new disposable item;

an operation element module to disable said electrical path by controlling said conducting element of said new disposable item to enter said second state in response to detection of said return signal by said operation status module, thereby indicating use of said new disposable item;

an operation verification module to re-transmit said status signal over said electrical path to said conducting element of said new disposable item in response to said disablement by said operation element module and to detect the absence of a return signal from said conducting element to verify placement of that conducting element in said second state by said operation element module, wherein said detection of the absence of said return signal by said operation verification module indicates an unused disposable item with said conducting element in said second state and said detection of said return signal by said operation verification module indicates a used disposable item utilizing a conductive member with said conducting element in said second state; and an operation disablement module to disable operation of said medical device in response to a used disposable item as indicated by said detection of said return signal by said operation verification module.

16. A method to determine prior use of a disposable item utilized with a medical device, wherein said disposable item includes a status device including a plurality of states with the state of said status device indicating a prior use of said disposable item and said medical device includes a processor coupled to said medical device and to said status device, said method comprising:

(a) receiving the disposable item within said medical device, wherein said status device includes a conducting element disposed within an electrical path extending between said status device and said processor, and wherein a first state of said conducting element enables said electrical path and indicates an unused disposable item, and a second state of said conducting element disables said electrical path and indicates prior use of that item; and (b) determining said prior use of said disposable item, via said processor, based on said status device state and controlling medical device operation in accordance with said prior use determination, wherein step (b) further includes:

(b.1) transmitting a status signal over said electrical path to said conducting element and detecting the presence of a return signal on said electrical path from said conducting element to determine said state of said conducting element and ascertain said prior use of said disposable item;

(b.2) disabling said electrical path by controlling said conducting element to enter said second state in response to detection of said return signal in step (b.1), thereby indicating use of said disposable item; and (b.3) re-transmitting said status signal over said electrical path to said conducting element in response to said disablement in step (b.2) and verifying placement of the conducting element in said second state, wherein the presence of an unused disposable item with said conducting element in said second state is determined in response to detection of the absence of said return signal, and wherein the presence of a used disposable item utilizing a conductive member with said conducting element in said second state is determined in response to detection of the presence of said return signal.

17. The method of claim 16, wherein said conducting element is a fuse, and step (b.2) further includes:

(b.2.1) placing said conducting element in said second state by transmitting a disablement signal of sufficient magnitude to disable said conducting element.

18. The method of claim 16, wherein step (b) further includes:

(b.4) enabling medical device operation in response to an unused disposable item as indicated by said detection of the absence of said return signal in step (b.3); and (b.5) disabling operation of said medical device in response to a used disposable item as indicated by detection of the absence of said return signal in step (b.1) or by said detection of said return signal in step (b.3).

19. The method of claim 18, wherein step (b) further includes:

(b.6) transmitting a status signal over said electrical path to said conducting element periodically during medical device operation enabled in step (b.4) and detecting the presence of a return signal on said electrical path from said conducting element to determine said state of said conducting element, wherein detection of said return signal indicates insertion of a new disposable item;

(b.7) disabling said electrical path by controlling said conducting element of said new disposable item to enter said second state in response to detection of said return signal in step (b.6), thereby indicating use of said new disposable item;

(b.8) re-transmitting said status signal over said electrical path to said conducting element of said new disposable item and detecting the absence of a return signal from said conducting element to verify placement of that conducting element in said second state in step (b.7), wherein said detection of the absence of said return signal indicates an unused disposable item with said conducting element in said second state and said detection of said return signal indicates a used disposable item utilizing a conductive member with a conducting element in said second state; and (b.9) disabling operation of said medical device in response to a used disposable item as indicated by said detection of said return signal in step (b.8).

20. An apparatus to determine prior use of a disposable item utilized with a medical device comprising:

status means secured to said disposable item for indicating a prior use of said disposable item and including a plurality of states, wherein the state of said status means indicates a prior use of said disposable item; and processing means coupled to said medical device and to said status means for determining said prior use of said disposable item based on said status means state and for facilitating control of medical device operation in accordance with said prior use determination, wherein said status means includes a conducting element disposed within an electrical path extending between said status means and said processing means with a first state of said conducting element enabling said electrical path and indicating an unused disposable item and a second state of said conducting element disabling said electrical path and indicating prior use of that item, and wherein said processing means includes:

status signal means for transmitting a status signal over said electrical path to said conducting element and for detecting a return signal on said electrical path from said conducting element to determine said state of said conducting element and ascertain said prior use of said disposable item;

element means for disabling said electrical path by controlling said conducting element to enter said second state in response to detection of said return signal by said status signal means, thereby indicating use of said disposable item; and verification means for re-transmitting said status signal over said electrical path to said conducting element in response to said disablement by said element means and for verifying placement of the conducting element in said second state by said element means, wherein said verification means determines the presence of an unused disposable item with said conducting element in said second state in response to detection of the absence of said return signal and determines the presence of a used disposable item utilizing a conductive member with said conducting element in said second state in response to detection of said return signal.

21. The apparatus of claim 20, wherein said conducting element is a fuse.

* * * * *